(12) United States Patent
Wang (10) Patent No.: US 8,501,290 B2
(45) Date of Patent: Aug. 6, 2013

(54) IMPLANTABLE MEDICAL DEVICES FABRICATED FROM POLYURETHANES WITH BIODEGRADABLE HARD AND SOFT BLOCKS AND BLENDS THEREOF

(75) Inventor: Yunbing Wang, Sunnyvale, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1488 days.

(21) Appl. No.: 12/014,714

(22) Filed: Jan. 15, 2008

(65) Prior Publication Data
US 2009/0182415 A1    Jul. 16, 2009

(51) Int. Cl.
*A61F 13/00* (2006.01)
*A61F 2/00* (2006.01)
*A61F 2/06* (2013.01)

(52) U.S. Cl.
USPC ........... 428/35.7; 424/423; 424/428; 623/1.1; 623/1.42; 623/1.46; 623/1.44

(58) Field of Classification Search
USPC ................ 435/128; 428/35.7; 424/426, 423, 424/428; 525/437; 623/1.1, 1.42, 1.46, 1.44
See application file for complete search history.

(56) References Cited

U.S. PATENT DOCUMENTS

| | | | |
|---|---|---|---|
| 5,665,831 A | 9/1997 | Neuenschwander et al. | |
| 6,245,103 B1 | 6/2001 | Stinson | |
| 6,475,477 B1 | 11/2002 | Kohn et al. | |
| 6,991,647 B2 * | 1/2006 | Jadhav | 623/1.2 |
| 7,691,402 B2 | 4/2010 | Guo et al. | |
| 7,842,737 B2 | 11/2010 | Wang et al. | |
| 7,956,100 B2 | 6/2011 | Wang | |
| 2001/0044651 A1 | 11/2001 | Steinke et al. | |
| 2004/0091982 A1* | 5/2004 | Gee et al. | 435/128 |
| 2004/0260386 A1 | 12/2004 | Shalaby | |
| 2005/0197422 A1 | 9/2005 | Mayadunne et al. | |
| 2005/0238683 A1 | 10/2005 | Adhikari et al. | |
| 2006/0292077 A1* | 12/2006 | Zhao | 424/9.4 |
| 2007/0155906 A1 | 7/2007 | Hissink et al. | |
| 2007/0225387 A1 | 9/2007 | Mayadunne et al. | |
| 2007/0231365 A1 | 10/2007 | Wang et al. | |
| 2007/0282426 A1 | 12/2007 | Wang et al. | |
| 2008/0033540 A1 | 2/2008 | Wang et al. | |
| 2008/0081063 A1 | 4/2008 | Wang et al. | |
| 2008/0107704 A1 | 5/2008 | Guo | |
| 2008/0147165 A1 | 6/2008 | Hossainy et al. | |
| 2008/0243228 A1 | 10/2008 | Wang et al. | |

(Continued)

FOREIGN PATENT DOCUMENTS

| | | |
|---|---|---|
| EP | 1 382 628 | 1/2004 |
| EP | 1 498 147 | 1/2005 |

(Continued)

OTHER PUBLICATIONS

Chen et al., Preparation and Characterization of biodegradable PLA polymeric blends, Feb. 18, 2002, Elsevier, 1167-1173.*

(Continued)

*Primary Examiner* — Ellen S Wood
(74) *Attorney, Agent, or Firm* — Squire Sanders (US) LLP (57) ABSTRACT

Medical devices, such as stents, fabricated at least in part from a polymer composite including a biodegradable elastomeric phase dispersed within a biodegradable polymeric matrix are disclosed. The composite is composed of a polyurethane block copolymer including soft polymer blocks and a hard polymer blocks.

19 Claims, 7 Drawing Sheets

U.S. PATENT DOCUMENTS

| | | |
|---|---|---|
| 2008/0247987 A1 | 10/2008 | Liggins et al. |
| 2008/0249608 A1 | 10/2008 | Dave |
| 2008/0249614 A1 | 10/2008 | Wang et al. |
| 2009/0081270 A9 | 3/2009 | Moore et al. |
| 2009/0099600 A1 | 4/2009 | Moore et al. |
| 2009/0175921 A1 | 7/2009 | Gunatillake et al. |
| 2009/0324675 A1 | 12/2009 | Gunatillake et al. |

FOREIGN PATENT DOCUMENTS

| | | |
|---|---|---|
| EP | 1 825 869 | 8/2007 |
| WO | WO 99/60920 | 12/1999 |
| WO | WO 2004/069097 | 8/2004 |
| WO | WO 2007/084444 | 7/2007 |
| WO | WO 2007/143116 | 12/2007 |
| WO | WO 2008/119973 | 10/2008 |

OTHER PUBLICATIONS

U.S. Appl. No. 11/729,506, filed Mar. 28, 2007, Wang et al.
U.S. Appl. No. 11/784,925, filed Apr. 9, 2007, Wang et al.
U.S. Appl. No. 11/810,464, filed Jun. 5, 2007, Wang et al.
U.S. Appl. No. 11/810,627, filed Jun. 5, 2007, Wang et al.
U.S. Appl. No. 11/864,729, filed Sep. 28, 2007, Wang.
Meredith et al., "LCST phase separation in biodegradable polymer blends: poly(D,L-lactide) and poly(ϵcaprolactone)", Macromol. Chem. Phys. 201, No. 6, pp. 733-739 (2000).
Miller et al., "Degradation Rates of Oral Resorbable Implants (Polylactates and Polyglycolates): Rate Modification with Changes in PLA/GPA Copolymer Ratios", J. Biomed. Mater. Res. vol. 11, pp. 711-719 (1977).
Wang et al., "Polyethylene-Poly(L-lactide) Diblock Copolymers: Synthesis and Compatibilization of Poly(L-lactide)/Polyethylene Blends", J. of Polymer Science vol. 39, pp. 2755-2766 (2001).
International Search Report for PCT/US2009/030460, mailed Mar. 31, 2010, 3 pgs.
International Search Report for PCT/US2008/077477, mailed Feb. 11, 2010, 2 pgs.
International Search Report for PCT/US2009/048040, mailed Sep. 17, 2010, 14 pgs.
International Search Report for PCT/US2009/038978, mailed Jul. 6, 2010, 4 pgs.
James et al., "Polyurethanes with radiopaque properties", Biomaterials 27, pp. 160-166 (2006).
Jayakrishnan et al., "Synthesis and Polymerization of Some Iodine-Containing Monomers for Biomedical Appllications", J. of Applied Pol. Science, vol. 44, pp. 743-748 (1992).
Kruft et al., "Studies on radio-apaque polymeric biomaterials with potential applications to endovascular prostheses", Biomat. vol. 17, No. 18, pp. 1803-1811 (1996).

* cited by examiner

IMPLANTABLE MEDICAL DEVICES FABRICATED FROM POLYURETHANES WITH BIODEGRADABLE HARD AND SOFT BLOCKS AND BLENDS THEREOF

BACKGROUND OF THE INVENTION

1. Field of the Invention

This invention relates to implantable medical devices fabricated from polyurethane block copolymers and methods of fabricating such implantable medical devices.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a constraining member such as a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil. In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

Potential problems with polymeric stents include that they may have inadequate toughness and they may have a degradation rate that is slower than is desirable for certain treatments.

SUMMARY OF THE INVENTION

Various embodiments of the present invention include a stent body fabricated at least in part from a polymer-polymer composite comprising a block copolymer, the block copolymer including: hard blocks and soft blocks, wherein the hard blocks and soft blocks are joined by di-urethane linkages, and wherein the material includes a biodegradable elastomeric phase dispersed within a biodegradable glassy polymeric matrix, wherein the elastomeric phase comprises the soft blocks and the matrix comprises the hard blocks, wherein the soft blocks are tougher than the hard blocks and the polymeric matrix at physiological conditions.

Additional embodiments of the present invention include a stent body fabricated at least in part from a polymer composite comprising a block copolymer blended with a matrix polymer, the block copolymer including: hard blocks and soft blocks, wherein the hard blocks and soft blocks are joined by di-urethane linkages, and wherein the polymer composite includes a biodegradable elastomeric phase dispersed within a biodegradable glassy polymeric matrix, the elastomeric phase comprising the soft blocks and the matrix phase comprising the matrix polymer and the hard polymer blocks, wherein the soft blocks are tougher than the hard blocks and the matrix polymer at physiological conditions.

Further embodiments of the present invention include a stent body fabricated at least in part from a polymer composite, the composite comprising block copolymer including: hard blocks and soft blocks, wherein the hard blocks and soft blocks are joined by di-urethane linkages, and wherein the polymer composite includes a biodegradable elastomeric phase dispersed within a biodegradable polymeric matrix, wherein the elastomeric phase comprises the soft blocks and the hard blocks make up all or substantially all of the polymeric matrix, wherein the soft blocks are tougher than the hard blocks and the polymeric matrix at physiological conditions.

Certain other embodiments of the present invention include a method of fabricating a stent comprising: allowing a hard polymer diol, a soft polymer diol, and a di-isocyanate to react to form a biodegradable polyurethane comprising hard polymer blocks and soft polymer blocks joined by di-urethane linkages; and forming a stent body comprising the polyurethane, wherein the soft blocks have a greater toughness than the hard blocks at physiological conditions.

DETAILED DESCRIPTION OF THE INVENTION

As used herein, an "implantable medical device" includes, but is not limited to, self-expandable stents, balloon-expandable stents, stent-grafts, and generally tubular medical devices.

An implantable medical device can be designed for the localized delivery of a therapeutic agent. A medicated implantable medical device may be constructed by coating the device or substrate with a coating material containing a therapeutic agent. The substrate of the device may also contain a therapeutic agent.

Figures 1A, 1B:
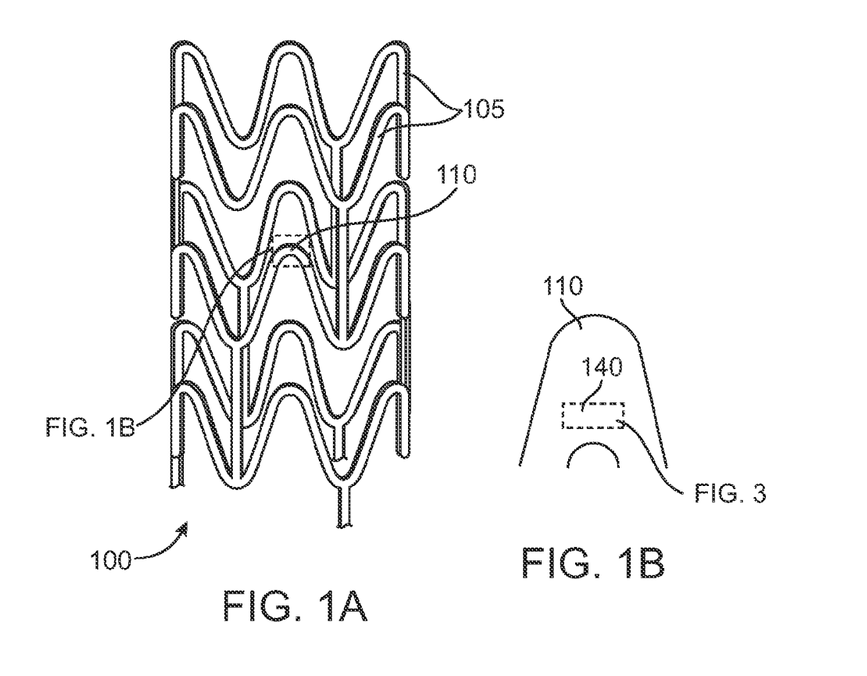
FIG. 1A depicts a stent.
FIG. 1B depicts a section of a structural element from the stent depicted in FIG. 1A.

FIG. 1A depicts a view of a stent 100. In some embodiments, a stent may include a body or scaffolding having a pattern or network of interconnecting structural elements 105. Stent 100 may be formed from a tube (not shown). The pattern of structural elements 110 can take on a variety of patterns. The structural pattern of the device can be of virtually any design. The embodiments disclosed herein are not limited to stents or to the stent pattern illustrated in FIG. 1A. The embodiments are easily applicable to other patterns and other devices. The variations in the structure of patterns are virtually unlimited. A stent such as stent 100 may be fabricated from a tube by forming a pattern with a technique such as laser cutting or chemical etching.

An implantable medical device can be made partially or completely from a biodegradable, bioabsorbable, or biostable polymer. A polymer for use in fabricating an implantable medical device can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes.

Some polymers that may be suitable for implantable medical devices such as stents have potential shortcomings. For example, some crystalline or semi-crystalline polymers may be selected primarily on the basis of strength and stiffness at physiological conditions so that the stent substrate or scaffolding can provide adequate support for a lumen. Physiological conditions refer to conditions within a human patient including, but not limited to, body temperature. Such polymers may be glassy or have a Tg above body temperature making them stiff and strong at body temperature which is approximately 37° C. A "glassy polymer" refers to a polymer having Tg above body temperature. One such shortcoming of such crystalline or semi-crystalline polymers is that their toughness is lower than desired, in particular, for use in stent applications. For example, polymers such as poly(L-lactide) (PLLA), polyglycolide (PGA), or copolymers thereof, poly (L-Lactide-co-glycolide) (PLGA), tend to be brittle under physiological conditions or conditions within a human body.

PGA, relative to other biodegradable polymers, is highly crystalline, with a crystallinity range reported in the range of 35-75%. The molecular and subsequent crystalline structure of PGA allow very tight chain packing and consequently give to the material some very unique mechanical, physical, and chemical properties (See Table 1 below). For example, its specific gravity is around 1.5-1.7 which is very high for a polymeric material. It also has a high melting point and low solubility in most organic solvents. PGA, which is the simplest linear aliphatic polyester, degrades by hydrolysis of the easily accessible and hydrolytically unstable aliphatic-ester linkages. The degradation time, usually a few months, depends on multiple factors like molecular weight, degree of crystallinity, crystal morphology, and physico-chemical characteristics of the environment.

While structurally very similar to PGA, PLLA has some quite different chemical, mechanical and physical properties due to the presence of a pendant methyl group on the alpha carbon. This makes the PLLA a chiral molecule and the D, L, and DL isomers are possible. PLLA are semicrystalline polymers, while D,L-PLA is a completely amorphous material. The methyl group in PLLA makes the carbonyl of the ester link sterically less accessible to hydrolytic attack, which, depending on certain factors like the type of PLLA, its molecular weight, and its degree of crystallinity, makes the PLLA typically more hydrolytically stable than PGA when exposed to the same environment.

Figure 2:
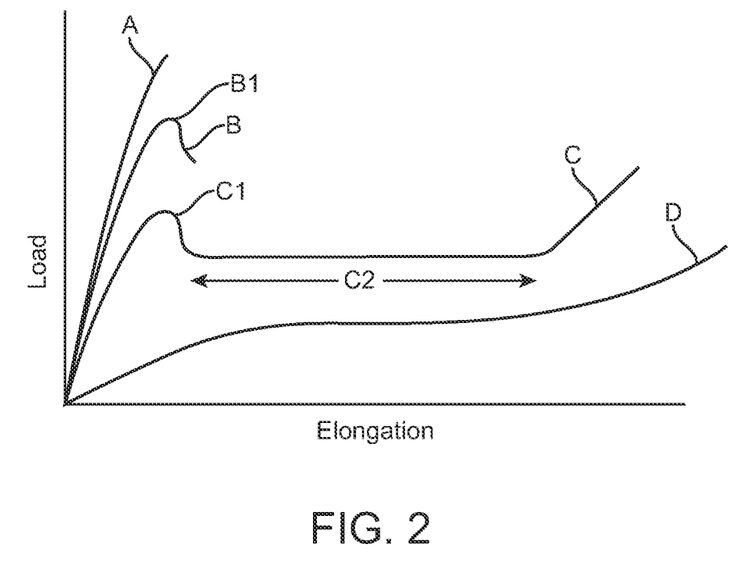
FIG. 2 represents the load-elongation curves for a typical polymer tested at four temperatures showing regions of mechanical behavior.

FIG. 2 represents the load-elongation curves for a typical polymer tested at four temperatures showing regions of mechanical behavior. Curve A is representative of a brittle fracture mechanism that occurs at low temperatures (below Tg). In curve A, the load rises approximately linearly with increasing elongation until a failure or a breaking point at the end of the curve. The elongation at the breaking point is typically less than 5%. In the behavior in curve A, there is little or no plastic deformation before failure. Curve B depicts a ductile fracture mechanism at higher temperatures in which a yield point B1 is observed after which the load falls before failure, typically between 10-20% elongation. Polymers exhibiting behavior shown in curves A and B can be very stiff (high modulus) and have a relatively high strength (load at failure). Such polymers have a relatively low toughness. Curve C represents the behavior of a polymer at still higher temperatures in which strain hardening occurs. After they yield point C1, the neck stabilizes and cold drawing ensues, as shown by flat region C2, with extensions up to 1000% often resulting. Curve D represents the behavior at even higher temperatures in which homogeneous, rubber-like deformation occurs, with a very large elongation at break. In an amorphous polymer, this rubber-like behavior occurs above the Tg, so the stress levels are very low.

As indicated below, one measure of toughness is the area under a stress-strain or load-elongation curve from zero strain to the strain at fracture. Therefore, the modulus, stress at fracture (strength), and elongation at fracture are relevant to the toughness of a polymer. For example, a polymer with a lower strength can have a higher toughness than a brittle polymer if it has a higher elongation at break and a lower modulus.

One way to increase fracture toughness of a low fracture toughness polymer under physiological conditions is to form a polymer-polymer composite that includes the low fracture toughness polymer blended with a polymer having a higher fracture toughness at physiological conditions. A "composite" refers generally to a material in which two or more distinct, structurally complementary substances combine to produce structural or functional properties not present in any individual components. The two or more distinct substances may be combinations of different classes of materials such as metals, ceramics, glasses, and polymers. The two or more substances can also be a combination two or more different polymers that form different phases.

In such a polymer-polymer composite, the low fracture toughness polymer is blended with another polymer having a higher or relatively high fracture toughness under physiological conditions. The higher fracture toughness polymer is also immiscible and forms a discrete or dispersed phase within the low fracture toughness polymer. The discrete phase can absorb energy arising from stress imparted to a device made from the composite to increase the fracture toughness of the device. To ensure good energy transfer between interfaces of the phases, it is important that there be sufficient bonding or adhesion between the phases. See, Y. Wang, etc. Journal of Polymer Science Part A: Polymer Chemistry, 39, 2001, 2755-2766.

Another shortcoming of some biodegradable polymers is their degradation rate can be slower or faster than desired for certain stent treatments. For instance, the degradation rate may be too slow. As a result, the degradation time of a stent made from such a polymer can be longer than desired. Reducing degradation time allows further surgery or intervention, if necessary, on a treated vessel to occur sooner. Additionally decreasing degradation time helps cut down on the cases of late stent thrombosis, a condition in which clots form on the surface of the stent months or years after deployment. For example, a stent made from PLLA can have a degradation time of between about two and three years or longer (See Table 1). "Degradation time" refers to the time for a stent implanted in a vessel to completely absorb. "Degradation time" can also refer to the time for a stent to completely absorb under in vitro conditions. In some treatment situations, a degradation time of less than a year may be desirable, for example, between six and 12 months, or more narrowly, between eight and ten months.

The degradation of a hydrolytically degradable polymer follows a sequence including water penetration into the polymer followed by hydrolysis of bonds in the polymer. Thus, the degradation of a polymer can be influenced by its affinity for water and the diffusion rate of water through the polymer. A hydrophobic polymer has a low affinity for water which results in a relatively low water penetration. In addition, the diffusion rate of water through crystalline regions of a polymer is lower than amorphous regions. Thus, as either the affinity of a polymer for water decreases or the crystallinity increases, water penetration and water content of a polymer decreases, resulting in a slower degradation rate.

Various embodiments of the present invention include an implantable medical device, such as a stent, fabricated at least in part of a polymer-polymer composite including a discrete polymer phase dispersed within a polymer matrix or continuous polymer phase. In some embodiments, the discrete phase polymer has a higher toughness than the matrix polymer. In such embodiments, the higher toughness polymer can have a higher elongation at break, a lower modulus, or both. In other embodiments, the discrete phase polymer has a higher degradation rate than the matrix polymer. In some embodiments, the discrete phase increases the toughness of the composite, increases the degradation rate of the composite, or increases both the toughness and degradation rate of the composite.

In exemplary embodiments, the higher toughness polymer can have an elongation at break at least 2, 4, 10, or at least 100 times greater or greater than 100 times greater than the polymer matrix. In other exemplary embodiments, the higher toughness polymer can have a modulus less than 20%, 50%, or less than 80% of the matrix polymer. In some exemplary embodiments, the degradation time of the higher toughness polymer can be less than 20%, 30%, 50%, or less than 80% of the degradation time of the matrix polymer.

Figure 3:
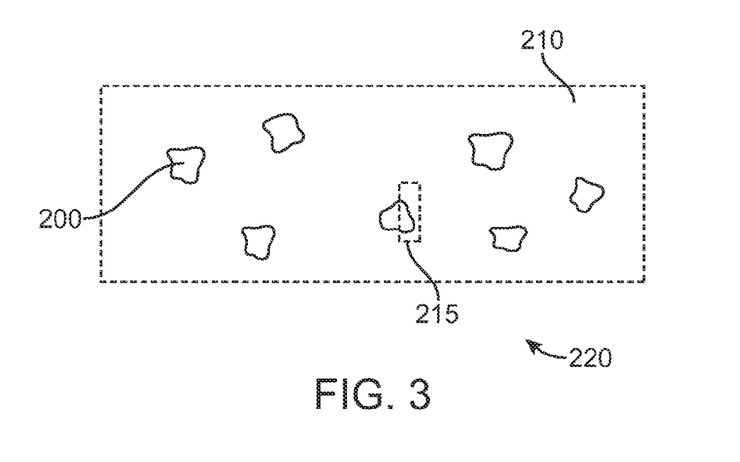
FIG. 3 depicts a schematic close-up view of the section depicted in FIG. 1B.

FIG. 1B depicts a section of a segment 110 of strut 105 from the stent depicted in FIG. 1A. FIG. 3 depicts a microscopic section 220 of a portion 140 of segment 110 of the strut as depicted in FIG. 1B. Portion 140 includes a discrete or dispersed phase 200 within a continuous phase 210.

Generally, a polymer-polymer or polymer blend exhibits properties that can markedly vary from those of the individual polymers. Macaúbas P. H., Demarquette N. R., Rheology as a Tool for Immiscible Polymer Blends Characterization: Interfacial tension and compatibilization, in RheoFuture. 2002, Thermo Electron Corporation: Karlsruhe, Germany. The higher fracture toughness polymer can enhance the fracture toughness of the composite. It is believed that when a device is placed under stress, the discrete phase tends to absorb energy when a fracture starts to propagate through a structural element. Crack propagation through the continuous phase may then be reduced or inhibited. As a result, fracture toughness of the composite, and thus structural elements of a device fabricated from the composite is increased. Thus, brittle polymers can be toughened by incorporating into their microstructure higher toughness components that can act as "stress concentrators", due to their lower tensile modulus. The embedded stress concentrators in the more brittle continuous phase permit elastic energy storage or ductile yield mechanisms that increase its resistance to fracture. Meredith J. C., Amis E. J., LCST phase separation in biodegradable polymer blends: poly(D,L-lactide) and poly(ε-caprolactone), Macromol. Chem. Phys., 2000. 201(6): p. 733-739.

In certain embodiments, the discrete phase has a polymer that is elastomeric. An "elastomeric" or "rubbery" polymer refers to a polymer which can resist and recover from deformation produced by force, as in natural rubber. In one embodiment, elastomers or rubbery polymers can be stretched repeatedly to at least twice their original length and, immediately upon release of the stress, return with force to their approximate original length. Elastomeric polymers tend to have a percent elongation at break larger than lower toughness polymers, such as brittle polymers.

In some embodiments, the low toughness polymer can be above its Tg when a device is implanted. In some embodiments, the low toughness polymer, such as an elastomeric polymer, of the dispersed phase has a Tg below body temperature. In other embodiments, the low toughness polymer of the dispersed phase has a Tg below ambient temperature. Ambient temperature can refer to a temperature between 20° C. and 30° C. Additionally, some elastomers or rubbery polymers are substantially or completely amorphous.

Various embodiments of the present invention include a stent body fabricated at least in part from a polymer-polymer composite including a polyurethane block copolymer that includes a hard polymer block and a soft polymer block, the soft polymer block having a higher toughness than the hard polymer block. In such embodiments, the hard blocks and soft blocks are joined by di-urethane linkages.

In some embodiments, the soft block is an elastomeric block. In such embodiments, the soft block has a toughness higher than the hard block at physiological conditions. The soft block can have a Tg below body temperature. In addition, the hard block or rigid block can be a glassy polymer block having a Tg above human body temperature. Furthermore, in these embodiments, the composite includes a biodegradable elastomeric phase dispersed within a biodegradable polymeric matrix or continuous phase, such that the elastomeric phase includes the soft blocks and the matrix or continuous phase includes the hard blocks.

In one set of embodiments, the composite can be a blend of the block copolymer and a matrix polymer. In such embodiments, the dispersed or discrete phase includes the soft blocks and the continuous phase includes the hard blocks and the matrix polymer. In another set of embodiments, the composite can include a block copolymer having hard blocks with molecular weights high enough such that the hard blocks make up a substantial portion or up to 100% of the matrix or continuous phase.

In all such embodiments, one or more structural elements or struts of a stent can be fabricated from the composite. In other such embodiments, the body, scaffolding, or substrate of a stent can be made from the composite. The body, scaffolding, or substrate may be primarily responsible for providing mechanical support to walls of a bodily lumen once the stent is deployed within the bodily lumen. A stent body, scaffolding, or substrate can refer to a stent structure with an outer surface to which no coating or layer of material different from that of which the structure is manufactured. If the body is manufactured by a coating process, the stent body can refer to a state prior to application of additional coating layers of different material. By "outer surface" is meant any surface however spatially oriented that is in contact with bodily tissue or fluids. A stent body, scaffolding, or substrate can refer to a stent structure formed by laser cutting a pattern into a tube or a sheet that has been rolled into a cylindrical shape.

In some embodiments, a majority, substantially all, or all of the stent body, scaffolding, or substrate can be made from the composite. Substantially all of the body can refer to greater than 90%, 95%, or greater than 99% of the body.

As mentioned above, the polyurethane block copolymer includes a hard polymer block and a soft polymer block joined by di-urethane linkages. The general form of such a polyurethane block copolymer is:

where $P_H$ is the hard block, $P_S$ is the soft block, NH(CO)O and O(CO)NH are urethane groups, and O(CO)NH—R—NH(CO)O is the di-urethane linkage. R is a functional group derived from a di-isocyanate which is one of the reactants used in the formation of the polyurethane block copolymer.

As described in more detail below, the polyurethane block copolymer can be formed by reacting a hard block polyol and a soft block polyol with a di-isocyanate (O=C=N—R—N=C=O). Various kinds of di-isocyanates can be used, such as aliphatic and aromatic di-isocyanates. Exemplary di-isocyanates include, but are not limited to, di-isocyanatomethane, di-isocyanatobutane, di-isocyanatoethane, di-isocyanatohexane, di-isocyanatocubane, lysine di-isocyanate, and di-isocyanatocyclohexane.

Generally, it is desirable for the discrete phase regions to be uniformly or substantially uniformly dispersed throughout the continuous polymer phase to facilitate the increase in toughness. The more dispersed the discrete phase regions, the greater is the increase in toughness. Additionally, the increase in toughness is related to the size of the discrete phase. Both the degree of dispersion and discrete phase size can be controlled by the length or molecular weight of the soft blocks. The characteristic length of a discrete phase can be 1 nm to 100 nm, 100 nm to 500 nm, 500 nm to 1,000 nm, or greater than 1,000 nm.

In some embodiments, the molecular weight of the soft blocks can be between about 0.2 kg/mol to 2 kg/mol to obtain a desired characteristic length of the discrete phase regions. In other embodiments, the molecular weight, Mn, of the soft blocks can be 2 kg/mol to 20 kg/mol, or greater than 20 kg/mol. In general, the soft blocks of the block copolymer are selected that have a higher fracture toughness than the matrix polymer. In some embodiments, the soft blocks can have a lower modulus, higher elongation at break, or both than the matrix polymer. In certain embodiments, the soft blocks can be include functional units or groups that form high fracture toughness or elastomeric polymers. Biodegradable polymers having a relatively high fracture toughness include, but are not limited to, polycaprolactone (PCL) and poly(trimethylene carbonate) (PTMC), polydioxanone (PDO), poly(4-hydroxy butyrate) (PHB), and poly(butylene succinate) (PBS). Thus, some embodiments of soft blocks can include CL, TMC, DO, HB, and BS monomers. The mechanical and degradation properties of some of these polymers are provided in Table 1.

Additionally, the hard blocks and the matrix polymer can be selected from polymers having a Tg greater than human body temperature. Exemplary hard block polymers include PLLA, PLGA, PGA and Polymandelide (PM).

In certain embodiments, the soft blocks can be selected that are faster eroding than the hard blocks and the matrix polymer. As a result, since the soft blocks are in the discrete phase, the soft blocks tend to increase the degradation rate of the composite. In such embodiments, the discrete phase can decrease the degradation time of a composite stent or a portion of a stent fabricated from the composite. In some embodiments, the degradation time of a composite stent can be less than 75%, 50%, 40%, or less than 25% of a stent fabricated from the matrix polymer.

In exemplary embodiments, the soft blocks can be selected to increase the toughness of a composite for a device. Additionally, the soft blocks can be selected to increase the degradation rate, and thus, decrease the degradation time of a device fabricated from the composite. Table 1 shows PCL and PDO polymers have a lower modulus and larger elongation at break than PLLA, PGA, and PLGA. PCL is an elastomeric polymer with a relatively low modulus and an elongation at break many times larger than PLLA, PGA, and PLGA. However, the degradation rate is similar to PLLA. Thus, a soft block containing CL is expected to increase the toughness, as shown by the higher elongation at break and lower modulus, but may not increase the degradation rate of a composite. PDO also has a lower modulus than PLLA, PGA, and PLGA, however, its elongation at break, although higher than these polymers, is much lower than PCL. However, PDO has a higher degradation rate than PCL. As result, a soft block including DO is expected to increase the degradation rate of the composite and decrease the degradation time of a composite made from the composite. As discussed below, the soft block can a copolymer or homopolymer.

The toughness and degradation rate can be tuned by the weight percent of the soft blocks in the composite.

As shown in Table 1, the PDO block has a much shorter degradation time than the PLLA, the PDO block can degrade within one year. Also, the degradation products of PDO and other elastomeric blocks are acidic and hydrophilic. Thus, as the PDO and these other elastomeric blocks erode, they will form acidic degradation products that will serve to enhance the degradation rate of hard blocks and matrix polymer such as PLLA. The degradation products are also hydrophilic, which will serve to increase the equilibrium level of moisture

TABLE 1

Properties of biodegradable polymers.

| Polymer | Melting Point (° C.)[1] | Glass-Transition Temp (° C.)[1] | Modulus (Gpa) | Tensile Strength (Mpa) | Elongation at break (%) | Degradation Time (months)[a] |
|---|---|---|---|---|---|---|
| PGA | 225-230[1] | 35-40 | 7.0[1] 5-7[2] | 60-80[2] | 30[4] | 6-12[1,2] |
| PLLA | 173-178[1] | 60-65 | 2.7[1] 3[2] | 60-70[2] | 3[4] | >24[1] >36[2] |
| PDLLA | Amorphous | 55-60 | 1.9[1] 2[2] | 2[2] | N/A | 12-16[1] 12-15[2] |
| PCL | 58-63[1] 60[4] | (−65)-(−60) | 0.4[1,2] 0.386[4] | 20-25[2] 4[4] | 800-1000[4] | >24[1] >36[2] |
| PDO | 110 | (−10)-0 | 1.5[1,2] | 30[2] | 35[3] | 6-12[1] 6[2] |
| PHB | 177[4] | N/A | 4[4] | 40[4] | 6[4] | |
| PGA-TMC | N/A | N/A | 2.4[1] | N/A | N/A | 6-12[1] |
| 85/15 PLGA | Amorphous | 50-55[1] | 2.0[1] | N/A | N/A | 5-6[1] |
| 75/25 PLGA | Amorphous | 50-55[1] | 2.0[1] | N/A | N/A | 4-5[1] |
| 65/35 PLGA | Amorphous | 45-50[1] | 2.0[1] | N/A | N/A | 3-4[1] |
| 50/50 PLGA | Amorphous | 45-50[1] | 2.0[1] | N/A | N/A | 1-2[1] |

[1]Medical Plastics and Biomaterials Magazine, March 1998.
[2]Medical Device Manufacturing & Technology 2005.
[3]The Biomedical Engineering Handbook, Joseph D. Bronzino, Ed. CRC Press in Cooperation with IEEE Press, Boca Raton, FL, 1995.
[4]Science, Vol. 297 p. 803 (2002)
[a]Degradation time also depends on part geometry.

Furthermore, the toughness and degradation rate of the composite depend upon the content (e.g., weight percent) of the soft block of the block copolymer. The toughness and degradation rate are expected to increase as the content of the soft block of the block copolymer increases. However, as the content increases, the flexibility of the composite is also expected to increase, with a simultaneous decrease in radial strength. Thus, the content of the soft block of the block copolymer can become so high that the radial strength of the composite can be too low for a stent scaffolding.

In some embodiments, the soft block can be a homopolymer. The homopolymer can be selected to provide a desired toughness (mechanical properties) and degradation rate for the composite. In an exemplary embodiment, the soft block can be a homopolymer of PCL, PDO, PHB, or PBS. Exemplary block copolymers include:

HO-(PLLA-O(CO)NH—R—NH(CO)O-PCL)$_n$-OH,

HO-(PLLA-O(CO)NH—R—NH(CO)O-PDO)$_n$-OH,

HO-(PLLA-O(CO)NH—R—NH(CO)O-PHB)$_n$-OH, 
or

HO-(PLLA-O(CO)NH—R—NH(CO)O-PBS)$_n$-OH.

in the polymer. Both of these mechanisms will increase the degradation rate of any implants manufactured from these materials. In addition, as soft blocks of the block copolymer erode, they will leave a porous structure behind, which serves to enhance the degradation rate of the stent structure.

In other embodiments, the soft block can be a copolymer. One advantage of a copolymer over a homopolymers soft block is that the presence of more than one functional group reduces crystallinity, which increases the degradation rate of the discrete phase. Thus, the degradation rate of the copolymer may have a degradation rate that is higher than the matrix polymer, which can decrease the degradation time of the composite. Another advantage of a copolymer is that the presence of more than one functional group allows an additional degree of freedom to tune the toughness or degradation rate of the discrete phase. Both the properties (mechanical properties, degradation rate or time) and the relative composition of a functional group can influence the properties of the composite.

As an example, Table 1 shows, a homopolymer soft block including CL may increase the toughness of a composite, but may not be capable to increasing the degradation rate a desired degree. Thus, the copolymer can include a functional group that enhances the toughness (high toughness functional group) and a functional group that increases the degradation rate (a fast degrading functional group). In particular, the soft block can include a fast degrading monomer that has a higher affinity for water and/or is more hydrolytically active than the high toughness functional group or the matrix polymer. In an exemplary embodiment, the soft block can include glycolide (GA) monomers which are faster degrading than a high toughness functional group, such as CL or TMC, and the matrix polymer, such as PLLA. Exemplary soft blocks can be P(GA-co-CL) or P(GA-co-TMC) random or alternating copolymer. Other examples include P(DO-co-CL) or P(DO-co-TMC). The faster degrading GA or DO monomers can increase the degradation rate of the polymer composite by increasing the equilibrium water content and penetration into the composite. Acidic and hydrophilic degradation products of the GA segments also act to increase the degradation rate of the composite. An exemplary block copolymer can include HO-(PLLA-O(CO)NH—R—NH(CO)O—P(GA-co-CL))$_n$-OH.

In some embodiments, the toughness and degradation rate of the discrete phase can be adjusted by the ratio of fast degrading and high toughness functional groups. As the ratio of CL, for example, increases in P(GA-co-CL) segments, the polymer becomes more flexible and tougher. Also, the Tg of the discrete phase segments can be tuned to a desired value by adjusting the ratio of component monomers. For example, the Tg of the discrete phase may be engineered to be less than a body temperature to provide a more flexible discrete phase under physiological conditions. Additionally, the degradation rate of the discrete phase, and thus the blend, can be increased by increasing the fraction of GA in the discrete phase segments. In exemplary embodiments, the P(GA-co-CL) segments can have greater than 1 wt %, 5 wt %, 20 wt %, or 40 wt % GA monomer.

In the first set of embodiments, the composite of the stent body includes a blend of the polyurethane block copolymer and a matrix polymer. In such embodiments, the discrete phase includes the soft block and the continuous phase includes the hard block and the matrix polymer. The hard block phase separates into matrix of the continuous phase and binds the discrete phase to the continuous phase, facilitating the increase in the fracture toughness of the polymer blend. In exemplary embodiments, the polymer blend or composite can include about 1-10 wt %, 10-30 wt %, or greater than 30 wt % of a block polymer and 70-99 wt % or less than 70 wt % of matrix polymer.

For example, one of the above-mentioned block copolymers:

is blended with PLLA. The PLLA hard block phase separates into the PLLA matrix polymer.

Additionally, in some embodiments, the weight percent of soft blocks is greater than hard blocks. In exemplary embodiments, the relative weight ratio of soft blocks to hard blocks may be 1-2, 2-5 or greater than 5. In other exemplary embodiments, the weight ratio of soft to hard blocks is in the range of 60:40 to 90:10, or more narrowly between 70:30 to 80:20. In some embodiments, the matrix polymer is a majority of the polymer blend, where majority means greater than 50 wt %. In further embodiments, the matrix polymer is greater than 60, 80, 90, or greater than 90 wt % of the polymer blend. In these embodiments, the soft block is immiscible with the matrix polymer, allowing for the formation of the discrete phase dispersed within the matrix polymer. The soft blocks of the discrete phase tend to increase the toughness of the composite.

Figure 4:
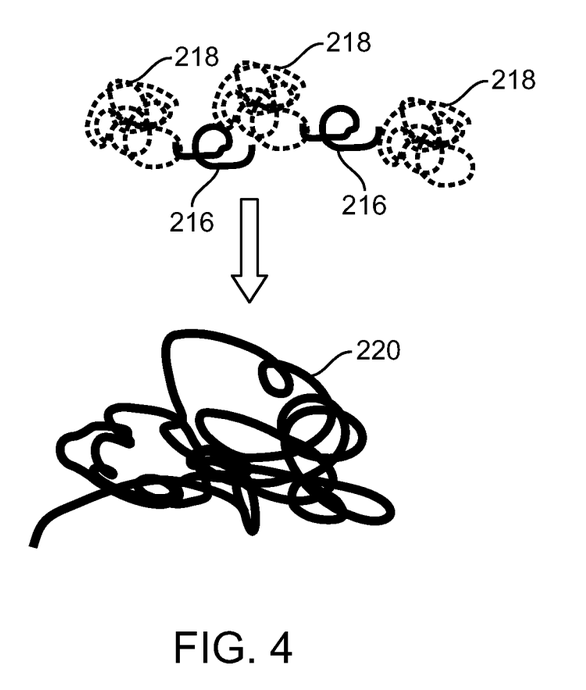
FIG. 4 depicts a schematic illustration of formation of a binary polymer blend.

FIG. 4 depicts a schematic illustration of formation of a binary blend of a block copolymer and a matrix polymer. A block copolymer 214 includes soft blocks 218 and hard blocks 216. Block copolymer 214 is blended with a matrix polymer 220, as shown by an arrow 217.

Furthermore, the hard blocks are miscible with the matrix polymer to allow the hard blocks to partially or completely phase separate into the continuous phase so that the hard blocks are within the continuous phase. In such embodiments, the chemical composition of the hard blocks is the same as the matrix polymer. In these embodiments, the hard blocks act as anchor segments that tend to increase the adhesion between the discrete phase and the continuous phase by binding the phases together. Thus, the hard blocks facilitate energy transfer between interfaces of the phases, allowing the discrete high toughness phase to increase the toughness of the composite. It is expected that the increase in toughness of the composite depends on the degree of adhesion between the continuous and discrete phases.

Figure 5:
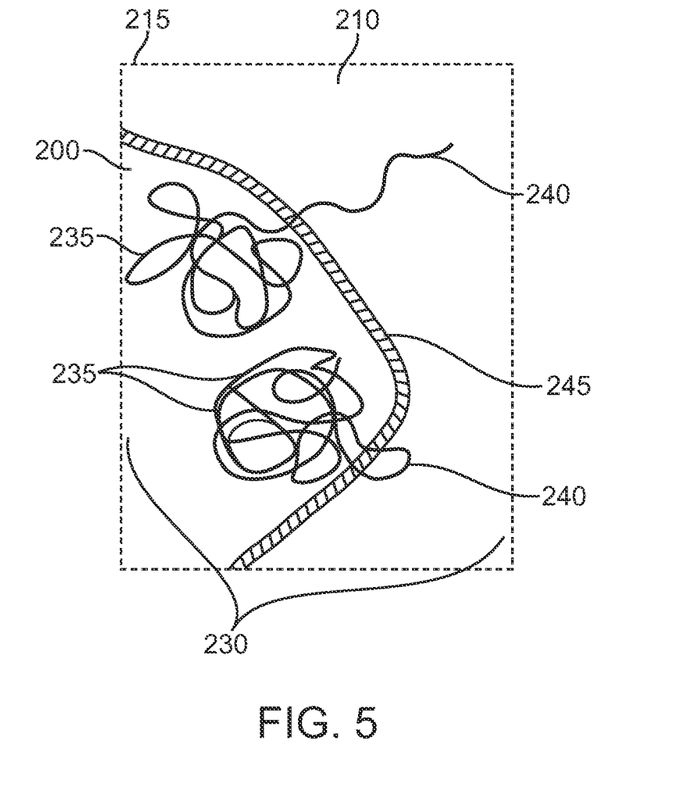
FIG. 5 depicts a schematic close-up view of an interface between a discrete polymer phase and a continuous polymer phase.

FIG. 5 depicts a schematic close-up view of section 250 including an interface between discrete phase 200 and continuous polymer phase 210. A block copolymer 230 includes soft blocks 235 and hard blocks 240. Line 245 is meant to delineate the boundary between discrete phase 200 and continuous phase 210. Hard blocks 240 are shown to be within continuous phase 210.

The composite can be formed by mixing or blending the block copolymer with a matrix polymer. The polymers can be blended using various mixing methods know in the art, for example, by mixing the polymer in an extruder. Representative examples of extruders include, but are not limited to, single screw extruders, intermeshing co-rotating and counter-rotating twin-screw extruders and other multiple screw masticating extruders.

In further embodiments, the matrix polymer can be a copolymer with functional groups selected to increase the degradation rate of the matrix polymer. Such a functional group can have a greater affinity for water or be more hydrolytically active than other functional groups of the copolymer. In an exemplary embodiment, the matrix copolymer can be poly(L-lactide-co-glycolide) (PLGA). Increasing the content of GA can increase the degradation rate of the PLGA since GA is more hydrolytically active than LLA. The weight percent of the GA in the copolymer can be at least about 1%, 5%, 10%, 15%, 30%, 40%, 50%, or greater 50%.

As the literature data in Table 1 shows, the degradation time of PLGA decreases from three to four years to less than six months as the GA content increases from 0 wt % to 50 wt %. PLGA is amorphous throughout a wide range of GA content due to the disruption in the regularity in the polymer chain by the addition of another monomer. The decrease in degradation time is due both to the decreased crystallinity and increased hydrolytic activity of the GA.

Figure 6:
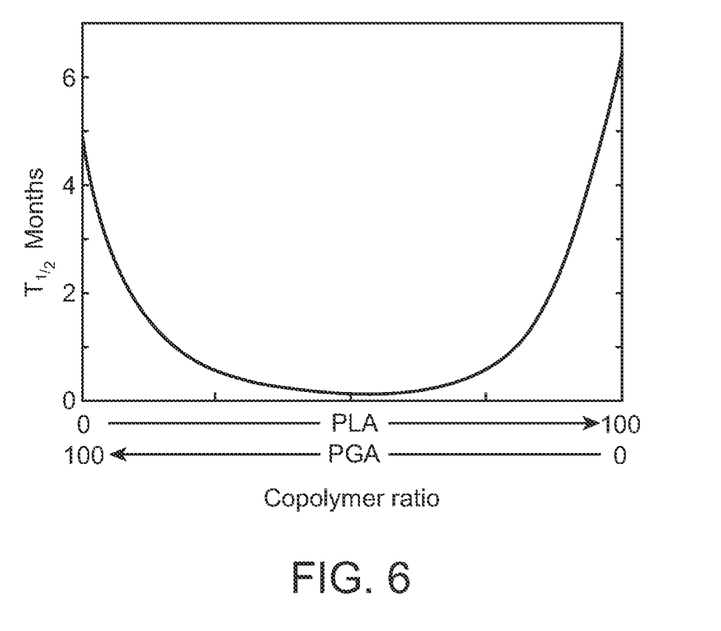
FIG. 6 shows the half-life of PLLA and PGA homopolymers and copolymers implanted in rat tissue.

Furthermore, as shown by FIG. 6, the linear relationship between the copolymer composition and the mechanical and degradation properties of the materials is not linear. FIG. 6 shows the half-life of PLLA and PGA homopolymers and copolymers implanted in rat tissue. Journal of Biomedical Materials Research, 11:711, 1977. The half-life in FIG. 6 refers to the amount of time for the modulus of a polymer to decrease by one half due to degradation of the polymer. For example, a copolymer of 50% GA and 50% LLA degrades faster than either homopolymer.

In some embodiments, the degradation time of the block copolymer composite can be reduced through the use of GA content in the matrix polymer. In other embodiments, the decrease in degradation time can be due both to GA content in the matrix polymer and the fast eroding discrete phase. In certain exemplary embodiments, the weight percent of GA and elastomeric content can be adjusted so that the degradation time of a stent scaffolding can be less than 24 months, 16 months, 12 months, or more narrowly, less than 12 months.

Additionally, the hard blocks of the block polymer can be selected so that the hard blocks are miscible with the matrix copolymer. In one embodiment, the hard blocks can have the same composition as the matrix copolymer. In another embodiment, the hard block can have a composition different from the matrix copolymer, but close enough so that the hard block is miscible with the matrix polymer. In another embodiment, the hard block can have composition different from the matrix polymer with the hard blocks being miscible with the matrix copolymer. For example, some embodiments can include a PLLA matrix polymer and PLGA hard blocks. Other embodiments can include a matrix polymer of PLGA and PLLA hard blocks or PLGA hard blocks.

Further embodiments include a composite including a polyurethane block copolymer having hard blocks that form all, part of, or substantially all of the matrix or continuous phase. Substantially all can refer to more than 95 wt % of the continuous phase. In such embodiments, the weight ratio of hard blocks to soft blocks is high enough such that the hard blocks can make up a majority, a substantial portion, or all of the matrix or continuous phase. For example, the hard blocks can make up more than 70, 80, 90, or greater than 90 wt % of the continuous phase.

In these embodiments, the hard blocks may be longer than the soft blocks described above. In certain embodiments, the molecular weight, Mn, of the hard blocks can be at least 1-2, 2-5, or more than 5 times the molecular weight of the soft blocks. In exemplary embodiments, the molecular weight of hard blocks can be 1-10 kg/mol, or greater than 10 kg/mol. In some embodiments, the matrix can be free of matrix polymers that are not a hard block of the block copolymer.

In these embodiments, the soft blocks can be homopolymers or random or alternating copolymers, as describe above. In exemplary embodiments, the long PLLA hard blocks can be bonded through di-urethane linkages to soft blocks including. In such exemplary embodiments, the polymeric material can include 1-30 wt %, or more narrowly, 5-20 wt % of the soft blocks and about 80-95 wt % of the hard PLLA blocks. In other exemplary embodiments, the weight ratio of soft to hard blocks is in the range of 1:99 to 30:70, or more narrowly, 5:95 to 20:80.

In further embodiments, the hard blocks of the block copolymer can be a random or alternating copolymer, such as PLGA. As indicated above, the GA content in the increases the degradation rate of the composite which decreases the degradation time of a composite stent. The content of GA in the hard blocks can be adjusted, alone or in combination with other parameters of the composite, so that the degradation time of a stent scaffolding can be less than 24 months, 16 months, 12 months, or less than 12 months.

Embodiments of the polyurethane block polymers described herein can be formed by solution-based polymerization. In other embodiments, such block copolymers can be formed through melt phase polymerization. In solution-based polymerization, in each of the synthesis steps the reactive components involved in the polymerization reaction are dissolved in a solvent. In melt phase polymerization, the reactions can take place, for example, in a mixing device such as extruder. As discussed above, the polyurethane block copolymer can be formed from a reaction of a hard block diol and a soft block diol with a di-isocyanate (O═C═N—R—N═C═O).

Figure 7:
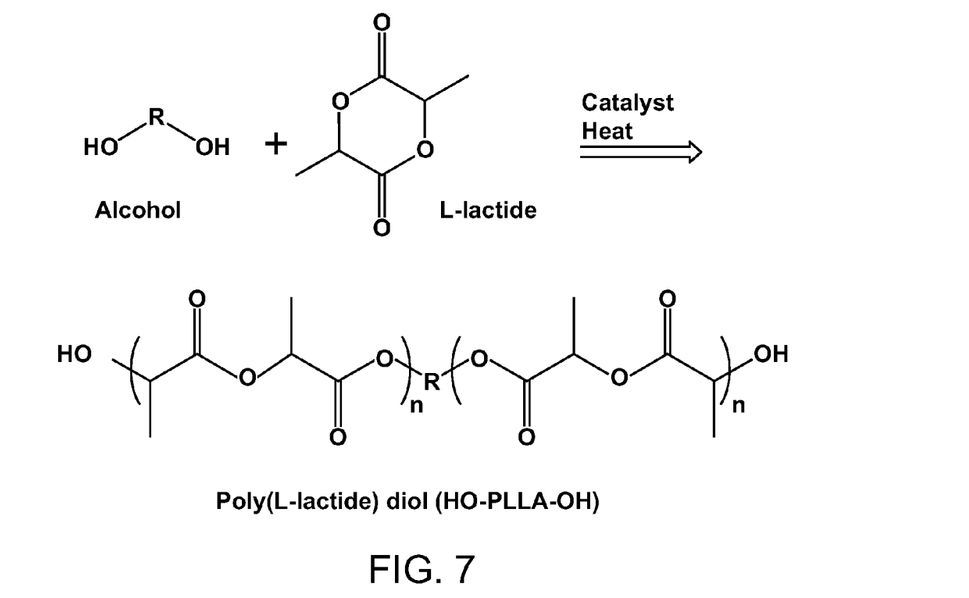
FIG. 7 depicts synthesis of PLLA diol.
Figure 8:
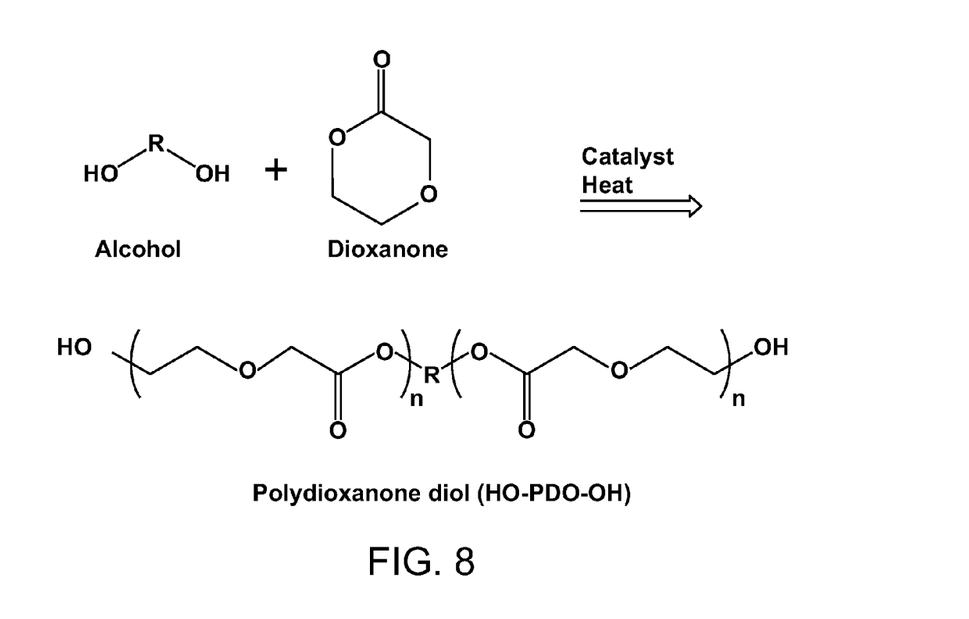
FIG. 8 depicts synthesis of PDO diol.

The hard block and soft block diols are prepared through reaction with a diol initiator component, i.e., an alcohol with two hydroxyl end groups. For example, the formation of a PLLA diol and a soft block PDO diol are illustrated by:

and where HO—R$_f$—OH is a diol initiator with a functional group R$_f$, HO-(LLA)$_n$-R$_f$-(LLA)$_n$-OH is a PLLA hard block diol which will be written as HO-PLLA-OH and HO-(DO)$_m$-R$_f$-(DO)$_m$-OH is a PDO soft block polyol which will be written as HO-PDO-OH. An exemplary diol initiator is ethylene glycol. The reactions occur in at an elevated temperature (greater than 100° C.) in a suitable solvent and in the presence of a suitable catalyst such a stannous octoate. The reactions are illustrated in FIGS. 7 and 8 for the hard block PLLA diol and the soft block PDO diol, respectively.

Figure 9:
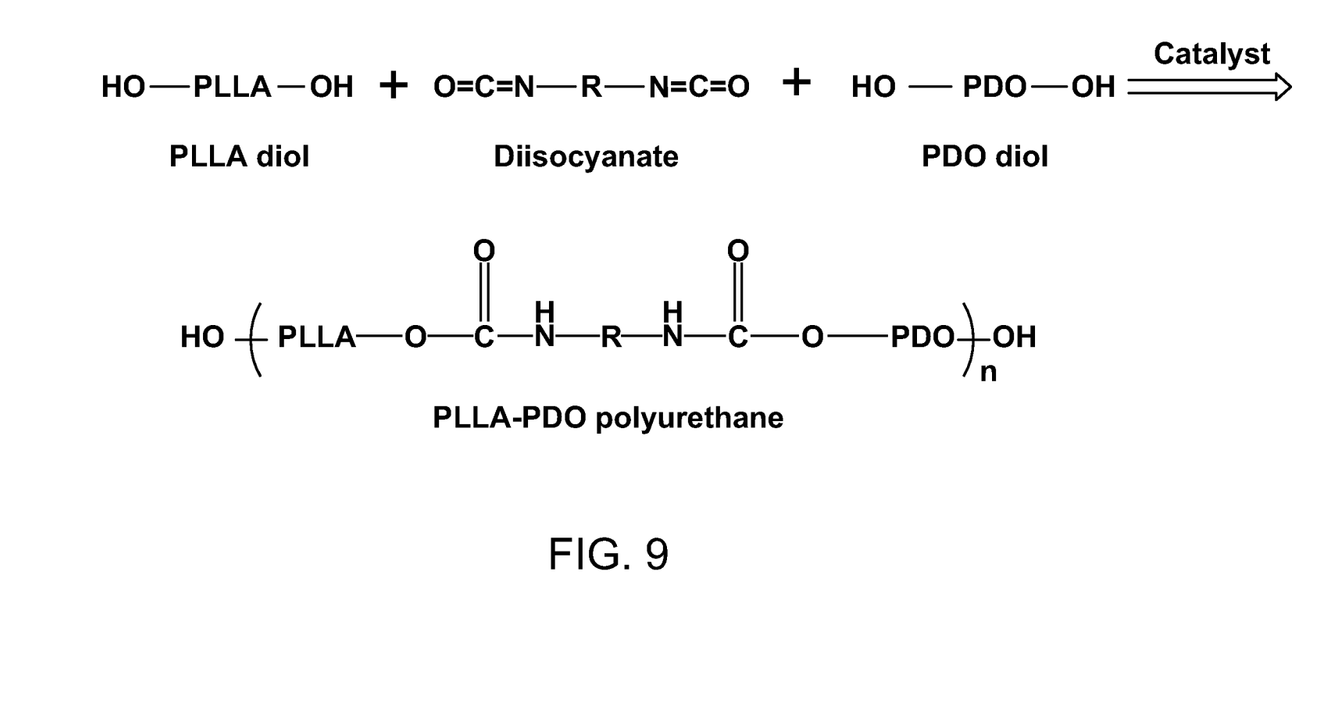
FIG. 9 depicts synthesis of a polyurethane block copolymer with PLLA hard blocks and PDO soft blocks.

The hard and soft diols are then allowed to react in solution with a di-isocyanate in the presence of a catalyst to form the polyurethane block copolymer. For example, the PLLA diol and PDO diol react as follows:

The reaction is further illustrated in FIG. 9. The reaction occurs at room temperature (20-30° C.) or at an elevated temperature (greater than room temperature) in a suitable solvent and in the presence of a suitable catalyst such a stannous octoate. Following synthesis of the block copolymer, the block copolymer is precipitated from the reaction solution by pouring the solution into a nonsolvent of the block copolymer. The strength, toughness, degradation rate of the composite, and a stent formed from the composite, can be controlled by the chain length and molar ratio of the hard block diol and the soft block diols.

As discussed above, the hard block in the block copolymer can be PLGA. For such embodiments, PLGA diols are used in the synthesis of the block copolymer. Additionally, various soft block homopolymers diols other than PDO diol may be used, such as PCL diol, PHB diol, PTMC diol etc. Also, soft block copolymer diols such as P(GA-co-CL) diol, P(GA-co-DO) diol, P(GA-co-TMC) diol, P(DO-co-CL) diol, etc. may be used to synthesize a block copolymer having such soft blocks.

Solvents used in the solution polymerization synthesis of the block copolymer include, but are not limited to, chloroform, THF, dioxane, toluene, xylene, and cyclohexane. Initiators include, but are not limited to, ethylene glycol, propylene glycol, butanediol and polyethylene glycol. Catalysts used to facilitate the synthesis of the block copolymer include, but are not limited to, stannous octoate, and stannous trifluoromethane sulfonate.

Embodiments of the composite disclosed herein may be formed into a polymer construct, such as a tube or sheet which can be rolled or bonded to form a tube. An implantable medical device can then be formed from the construct. For example, a stent can be fabricated from a tube by laser machining a pattern in to a tube. In another embodiment, a polymer construct may be formed from the composite mixture using an injection molding apparatus.

As indicated above, it is important for a stent to have high radial strength so that once it is deployed from the crimped state, it can support a lumen. In general, deforming a polymer construct can strengthen the polymer of the construct along an axis of deformation. In some embodiments of fabricating a stent from a polymer tube, the polymer tube can be radially expanded to increase the radial strength of the tube. The stent can then be fabricated from the polymer tube in its expanded state. Additionally, it has been observed that radially deforming a tube prior to cutting stent patterns increases the toughness of the stent scaffolding. In particular, the radial deformation reduces or eliminates cracks and breaking of the stent struts.

Representative examples of polymers that may be used to fabricate an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(L-lactide-co-glycolide); poly(D,L-lactide), poly(caprolactone), poly(trimethylene carbonate), polyethylene amide, polyethylene acrylate, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Additional representative examples of polymers that may be especially well suited for use in fabricating an implantable medical device according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol. For the purposes of the present invention, the following terms and definitions apply:

As indicated above, an implantable medical device such as a stent can be medicated by incorporating an active agent in a coating over the device or within the substrate of the device.

For the purposes of the present invention, the following terms and definitions apply:

"Molecular weight" can refer to the molecular weight of individual segments, blocks, or polymer chains. "Molecular weight" can also refer to weight average molecular weight or number average molecular weight of types of segments, blocks, or polymer chains. The number average molecular weight (Mn) is the common, mean, average of the molecular weights of the individual segments, blocks, or polymer chains. It is determined by measuring the molecular weight of N polymer molecules, summing the weights, and dividing by N:

$$\overline{M}_n = \frac{\sum_i N_i M_i}{\sum_i N_i}$$

where Ni is the number of polymer molecules with molecular weight Mi. The weight average molecular weight is given by $$\overline{M}_w = \frac{\sum_i N_i M_i^2}{\sum_i N_i M_i}$$

where Ni is the number of molecules of molecular weight Mi.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

"Stress" refers to force per unit area, as in the force acting through a small area within a plane. Stress can be divided into components, normal and parallel to the plane, called normal stress and shear stress, respectively. True stress denotes the stress where force and area are measured at the same time. Conventional stress, as applied to tension and compression tests, is force divided by the original gauge length.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. For example, a material has both a tensile and a compressive modulus. A material with a relatively high modulus tends to be stiff or rigid. Conversely, a material with a relatively low modulus tends to be flexible. The modulus of a material depends on the molecular composition and structure, temperature of the material, amount of deformation, and the strain rate or rate of deformation. For example, below its Tg, a polymer tends to be brittle with a high modulus. As the temperature of a polymer is increased from below to above its Tg, its modulus decreases.

"Strain" refers to the amount of elongation or compression that occurs in a material at a given stress or load.

"Elongation" may be defined as the increase in length in a material which occurs when subjected to stress. It is typically expressed as a percentage of the original length.

Elongation to Break is the strain on a sample when it breaks. It is usually is expressed as a percent.

"Toughness" is the amount of energy absorbed prior to fracture, or equivalently, the amount of work required to fracture a material. One measure of toughness is the area under a stress-strain curve from zero strain to the strain at fracture. The stress is proportional to the tensile force on the material and the strain is proportional to its length. The area under the curve then is proportional to the integral of the force over the distance the polymer stretches before breaking. This integral is the work (energy) required to break the sample. The toughness is a measure of the energy a sample can absorb before it breaks. There is a difference between toughness and strength. A material that is strong, but not tough is said to be brittle. Brittle substances are strong, but cannot deform very much before breaking.

"Solvent" is defined as a substance capable of dissolving or dispersing one or more other substances or capable of at least partially dissolving or dispersing the substance(s) to form a uniformly dispersed solution at the molecular- or ionic-size level at a selected temperature and pressure. The solvent should be capable of dissolving at least 0.1 mg of the polymer in 1 ml of the solvent, and more narrowly 0.5 mg in 1 ml at the selected temperature and pressure, for example, ambient temperature and ambient pressure.

EXAMPLES

The examples and experimental data set forth below are for illustrative purposes only and are in no way meant to limit the invention. The following examples are given to aid in understanding the invention, but it is to be understood that the invention is not limited to the particular materials or procedures of examples. The Examples below are provided by way of illustration only and not by way of limitation. The parameters and data are not to be construed to limit the scope of the embodiments of the invention.

Examples 1-4

Synthesis of Polyurethane Block Copolymer for Composite Without Blending with Matrix Polymer and Stent Preparation

Example 1

Synthesis of PLLA Diol Oligomer (Mn=2000 g/mol)

In this example, ethylene glycol (Mn=62 g/mol) as initiator, LLA as monomer, and stannous octoate as catalyst are used.

1000 g LLA, 16 g ethylene glycol (0.25 mol), and 250 mg stannous ocotate are added into a reactor free of moisture and oxygen. All chemicals are heated to 130° C. for 12 h to obtain PLLA diol oligomer.

Example 2

Synthesis of PDO Diol Oligomer (Mn=1000 g/mol)

In this example, ethylene glycol as initiator, DO as monomer, and stannous octoate as catalyst are used.

100 g DO, 3.1 g ethylene glycol (0.05 mol), and 25 mg stannous ocotate are added into a reactor free of moisture and oxygen. All chemicals are heated to 130° C. for 12 h to obtain PDO diol oligomer.

Example 3

Synthesis of Polyurethane Block Copolymer with PLLA Hard Blocks and PDO Soft Blocks In this example, PLLA diol, PDO diol as oligomers, diisocyanatobutane (Mn=140 g/mol) as connector, stannous octoate as catalyst are used.

Step 1: 1000 g PLLA diol, 100 g PDO diol, 42 g diisocyanatobutane (0.3 mol), 3 L anhydrous tetrahydrofuran (THF), and 250 mg stannous ocotate are added into a reactor free of moisture and oxygen. All chemicals are stirred at 60° C. for 24 h to obtain PLLA/PDO polyurethane with PLLA as a dominate component.

Step 2: The final polymerization solution is precipitated into 8 L methanol, filtered out and dried in vacuum at 80° C. until constant weight.

Example 4

Stent Preparation from the Synthesized PLLA/PDO Polyurethane

Step 1: Extrude tubes with designated inside diameter (ID) and outside diameter (OD) (0.02" and 0.07") from the synthesized PLLA/PDO polyurethane using a signal screw extruder at 190° C.

Step 2: Expand the extruded tubes to improve its mechanical property along the axial and radial directions.

Step 3: Cut stents from the expanded tubes by femto second laser and sterilize all stents after crimping.

Examples 5-8

Synthesis of Polyurethane Block Copolymer for Blending with PLLA Matrix Polymer and Stent Preparation

Example 5

Synthesis of PLLA Diol Oligomer (Mn=2000 g/mol)

In this example, ethylene glycol (Mn=62 g/mol) as initiator, LLA as monomer, and stannous octoate as catalyst are used.

10 g LLA, 0.155 g ethylene glycol (2.5 mmol), and 2.5 mg stannous ocotate are added into a reactor free of moisture and oxygen. All chemicals are treated to 130° C. for 12 h to obtain PLLA diol oligomer.

Example 6

Synthesis of PDO Diol Oligomer (Mn=2000 g/mol)

In this example, ethylene glycol as initiator, DO as monomer, and stannous octoate as catalyst are used. 100 g DO, 1.55 g ethylene glycol (25 mmol), and 25 mg stannous ocotate are added into a reactor free of moisture and oxygen. All chemicals are heated to 130° C. for 12 h to obtain PDO diol oligomer.

Example 7

Synthesis of Polyurethane Block Copolymer with PLLA Hard Blocks and PDO Soft Blocks In this experiment, PLLA diol, PDO diol as oligomers, diisocyanatobutane (Mn=140 g/mol) as connector, stannous octoate as catalyst are used.

Step 1: 10 g PLLA diol, 100 g PDO diol, 3.85 g diisocyanatobutane (27.5 mmol),
100 mL anhydrous THF, and 25 mg stannous ocotate are added into a reactor free of moisture and oxygen. All chemicals are stirred at 60° C. for 24 h to obtain elastic PLLA/PDO polyurethane with PDO as a dominate component.

Step 2: The final polymerization solution is precipitated into 1 L methanol, filtered out and dried in vacuum at 80° C. until constant weight.

Example 8

Stent Preparation from the Blend of PLLA and Polyurethane Block Copolymer

Step 1: Mix 1000 g PLLA and 100 g polyurethane and extrude them at 190° C. through a twin screw extruder to prepare compound.

Step 2: Extrude tubes with designated ID and OD (0.02" and 0.07") using the obtained compound through a signal screw extruder at 190° C.

Step 3: Expand the extruded tubes to improve mechanical properties along the axial and radial directions.

Step 4: Cut stents from the expanded tubes by femto second laser and sterilize all stents after crimping.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent body fabricated at least in part from a polymer-polymer composite comprising a block copolymer, the block copolymer including:
    hard blocks and soft blocks,
    wherein the hard blocks and soft blocks are joined by di-urethane linkages, and
    wherein the composite includes a biodegradable elastomeric phase dispersed within a biodegradable glassy polymeric matrix, wherein the elastomeric phase comprises the soft blocks and the matrix comprises a polymer having the same composition as the hard blocks, wherein the soft blocks are tougher than the hard blocks and the polymeric matrix at physiological conditions.

2. The stent body of claim 1, wherein the di-urethane linkages comprise urethane groups linked by a functional group selected from the group consisting of aliphatic functional group and aromatic functional group.

3. The stent body of claim 1, wherein the soft blocks are selected from the group consisting of polycaprolactone (PCL), poly(trimethylene carbonate) (PTMC), polydioxanone (PDO), and poly(4-hydroxy butyrate) (PHB) and wherein the hard blocks are selected from the group consisting of poly(L-lactide) (PLLA) and polyglycolide (PLGA).

4. The stent body of claim 1, wherein the soft blocks are selected from the group consisting of P(CL-co-GA), P(TMC-co-GA), P(DO-co-CL), and P(DO-co-GA) and wherein the hard blocks are selected from the group consisting of PLLA or PLGA.

5. The stent body of claim 1, wherein the hard blocks have a Tg above body temperature and the soft blocks have a Tg below body temperature.

6. The stent body of claim 1, wherein a degradation rate of soft blocks is faster than the hard blocks and the polymeric matrix, wherein the degradation of the soft blocks decreases the degradation time of the stent body.

7. The stent body of claim 1, wherein the block copolymer increases the adhesion between the polymer matrix and the elastomeric phase so that the elastomeric phase can increase the toughness of the stent body.

8. The stent body of claim 1, wherein the polymeric matrix further comprises a matrix polymer, the matrix polymer being blended with the block copolymer, wherein the hard blocks are miscible with the matrix polymer.

9. The stent body of claim 1, wherein the hard blocks comprises greater than 95 wt % of the polymer matrix.

10. A stent body fabricated at least in part from a polymer composite comprising a block copolymer blended with a matrix polymer, the block copolymer including:
    hard blocks and soft blocks,
    wherein the hard blocks and soft blocks are joined by di-urethane linkages, and
    wherein the polymer composite includes a biodegradable elastomeric phase dispersed within a biodegradable glassy polymeric matrix, the elastomeric phase comprising the soft blocks and the matrix phase comprising the matrix polymer and the hard polymer blocks, wherein the soft blocks are tougher than the hard blocks and the matrix polymer at physiological conditions.

11. The stent body of claim 10, wherein the soft block is selected from the group consisting of PCL, PTMC, PHB, and PDO and wherein the hard blocks are selected from the group consisting of PLLA or PLGA.

12. The stent body of claim 10, wherein the soft blocks are selected from the group consisting of P(CL-co-GA), P(TMC-co-GA), P(DO-co-CL), and P(DO-co-GA) and wherein the hard blocks are selected from the group consisting of PLLA or PLGA.

13. The stent body of claim 10, wherein the hard blocks and the matrix polymer have a Tg above body temperature and the soft block has a Tg below body temperature.

14. The stent body of claim 10, wherein a degradation rate of the soft block is faster than the hard block and the matrix polymer, wherein degradation of the soft blocks decreases the degradation time of the stent body.

15. The stent body of claim 10, wherein the hard block of the block copolymer increases adhesion between the matrix and the elastomeric phase so that the elastomeric phase can increase the toughness of the stent body.

16. The stent body of claim 10, wherein the matrix polymer and the hard block comprise PLLA and the soft block is selected from the group consisting of PCL, PTMC, PHB, PDO, P(CL-co-GA), P(TMC-co-GA), P(DO-co-CL), and P(DO-co-GA).

17. A stent body fabricated at least in part from a polymer composite, the composite comprising block copolymer including:
    hard blocks and soft blocks,
    wherein the hard blocks and soft blocks are joined by di-urethane linkages, and
    wherein the polymer composite includes a biodegradable elastomeric phase dispersed within a biodegradable polymeric matrix, wherein the elastomeric phase comprises the soft blocks and the hard blocks make up all or substantially all of the polymeric matrix, wherein the soft blocks are tougher than the hard blocks and the polymeric matrix at physiological conditions.

18. The stent body of claim 17, wherein the hard blocks are selected from the group consisting of PLLA and PLGA, and wherein the soft blocks are selected from the group consisting of PCL, PTMC, PHB, and PDO.

19. The stent body of claim 17, wherein the soft blocks are selected from the group consisting of P(CL-co-GA), P(TMC-co-GA), P(DO-co-CL), and P(DO-co-GA) and wherein the hard blocks are selected from the group consisting of PLLA or PLGA.

* * * * *